(12) United States Patent
Fukushima

(10) Patent No.: US 6,358,623 B1
(45) Date of Patent: Mar. 19, 2002

(54) TREATMENT FOR SURFACE TREATMENT AND CLEANING WHICH CONTAINS EUCALYPTUS OIL, AND WOODEN BUILDING MATERIAL IMPREGNATED WITH SAID TREATMENT

(75) Inventor: Saburo Fukushima, Osaka (JP)

(73) Assignee: Kabushiki Kaisha Nihon Tekuma, Osaka (JP)

( * ) Notice: Subject to any disclaimer, the term of this patent is extended or adjusted under 35 U.S.C. 154(b) by 0 days.

(21) Appl. No.: 09/284,407

(22) PCT Filed: Aug. 21, 1998

(86) PCT No.: PCT/JP98/03726

§ 371 Date: Apr. 12, 1999

§ 102(e) Date: Apr. 12, 1999

(87) PCT Pub. No.: WO99/09826

PCT Pub. Date: Mar. 4, 1999

(30) Foreign Application Priority Data

Aug. 21, 1997 (JP) .............................. 9-241836
Dec. 22, 1997 (JP) .............................. 9-365658

(51) Int. Cl.$^7$ .......................... C08L 91/00; C08L 91/06
(52) U.S. Cl. ...................... 428/543; 106/245; 106/268; 428/484; 428/497
(58) Field of Search ................................ 428/402, 543, 428/484, 497; 106/660, 661, 124.2, 220, 224, 230, 231, 245, 268

(56) References Cited

U.S. PATENT DOCUMENTS

| 4,013,475 | A | * | 3/1977 | Liebowitz et al. | .......... 106/271 |
| 4,590,302 | A | * | 5/1986 | Scheidl et al. | ............... 568/665 |
| 5,112,394 | A | * | 5/1992 | Miller | ............................ 106/3 |
| 5,661,159 | A | * | 8/1997 | Grieveson et al. | .......... 514/784 |
| 5,888,957 | A | * | 3/1999 | Durbut et al. | ............... 510/242 |

FOREIGN PATENT DOCUMENTS

| DE | 197 00 969 A1 | 7/1998 |
| JP | 61-244366 | 10/1986 |
| JP | 63-264510 | 11/1988 |
| JP | 2-129108 | 5/1990 |
| JP | 4-105605 | 4/1992 |
| JP | 4-106200 | 4/1992 |
| JP | 4-139104 | 5/1992 |
| JP | 5-39203 | 2/1993 |
| JP | 6-135812 | 5/1994 |
| JP | 6-237979 | 8/1994 |

* cited by examiner

Primary Examiner—Hoa T. Le
(74) Attorney, Agent, or Firm—William J. Sapone; Coleman Sudol; Sapone P.C.

(57) ABSTRACT

Cineole $C_{10}H_{18}O$ is used for as treatment agent for surface-treating wooden building materials. Eucalyptus oil mainly containing cineole may be utilized for the solution as a substitute. Japan wax, beeswax, carnauba wax or nonionic surface active agent is available as the additives of the agent. Since cineole has various pharmaceutical effects, wooden building materials impregnated therewith may exhibit preservability and protecting effects from molding and infesting with insects without spoiling natural appearance of wood, besides may contribute to present floorboards being sanitary and hygienic especially in humid climates.

3 Claims, No Drawings

TREATMENT FOR SURFACE TREATMENT AND CLEANING WHICH CONTAINS EUCALYPTUS OIL, AND WOODEN BUILDING MATERIAL IMPREGNATED WITH SAID TREATMENT

TECHNICAL FIELD OF THE INVENTION

The present invention relates to treatment agent for surface-treating and/or cleaning and wooden building materials impregnated with the treatment agent, more particularly, to the treatment agent, made of natural materials, for surface-treating and/or cleaning articles and structures disposed in and/or assembled into houses and buildings, and to the building materials like floorboards treated with said treatment agent, which are useful and unstimulative to skin of human beings and exhibit natural pharmaceutical effects, protecting effects from molding and from infesting with insects, ability of waterproofing and cleaning.

PRIOR ART

Recently, even in community facilities like hotels and halls flooring made of wooden materials has been actively adopted. One of the reasons is that wooden floor is more comfortable to walk on than synthetic resin products, e.g., vinyl chloride panel, another is that the introduction of wooden products matches with current life of natural-oriented type. On the other hand, walking with shoes on is unavoidable in lobbies and on passageways of the facilities being highly public, therefore their floorboards are needed high durability and high wear proof. In result, natural materials like Japanese cypresses and elm trees not only have been introduced but often coated on their surfaces with materials having the function of increase of wear proof and water proof.

The surfaces of wooden floorboards, being used under the circumstances of walking with shoes on and/or of coming and going frequently, are coated in, e.g., at least three layers by urethane. However, they do not often result in withstanding long-term use because of decrease of natural air permeability based on covering the surfaces thereof with opaque films and because of stagnating humidity beneath the floorboards.

In consideration of that there are few customs of walking with shoes on in rooms in Japan or most of countries of Asia, and of that a wet climate often continues for a long period, multi-layers coating mentioned above is inappropriate in the case that wooden materials are applied to floors of rooms, passages in houses and floors of hotels and gymnasiums. Because the surface structure of floorboards coated in multi-layers does not result in matching with peculiar climates by means of hindering natural breathing, i.e., humid controllability of boards. Moreover, it will become undesirable that smooth and comfortable touch of floorboards without spoiling the originality of wood is given during walking barefooted or with slippers.

Recently, performances of heat insulation and air-tightness of houses have been quickly improved, therefore, chemical substances contained in building materials, etc., often tends to cause chemical substances allergy, e.g., a headache, nausea and dizziness and so on, sick house syndrome group and cutaneous inflammation of atopic diseases, etc. As a matter of course, the concern about such problems has been so deep that it should been solved soon. It has been desired that natural materials is actively adopted for floorboards used in houses and buildings aiming at natural-oriented life, and extremely to say, leaving original woody characteristic on the surfaces thereof.

Meanwhile, it is indispensable for the surfaces not to be stained even if coffee, wine or soy-source spills on them. Nowadays, coating with wax or oil of natural materials has been widely noticed. From this background, as treatment agent of natural materials for coating on floorboards, etc., coconut oil and linseed oil have begun to use.

Needless to say, the coconut oil mentioned above is extracted from coconuts, of course, being very fatty. It has a disadvantage decreasing the air permeability of wooden floorboard though being vegetable oil. In addition, its melting point is rather high so that a coating work is not always easy for home working.

On the other hand, linseed oil which exists in flax seeds, is well-known to be used as substitute materials for making paint, wax, linoleum, printing ink and rubber. Though this is a kind of oil, its oil ingredient is only 30% to 40% at most and its characteristic is similar to wax. When such linseed oil is coated on floorboard, thereafter the floorboard will be as if to be waxed, keeping the surface thereof dry, on the other hand, resulting in decrease of the effect for dispersing moisture existing in boards, i.e., in inhibition of the air permeability thereof. Moreover, it is said that wax is characteristic of absorbing dust in the atmosphere, the appearance of improved products and/or substitutes is ,therefore, desired.

Incidentally, since there are few suitable treatment agents for treating or washing surfaces of tatami mats made of knitted rush up to recently, the tatami mats are ordinarily cleaned by wiping only with cloth wetted by pure water, resulting in being clammy on the surfaces thereof for a short time thereafter. It is really expected to be possible to walk barefooted without feeling uncomfortable even just after treated and/or wiped. And it is also desired to prevent ticks from breeding and sundry bacteria from propagating in the mats so as to solve the most serious problems relating to daily life on tatami mats.

The first object of the present invention is to provide treatment agents for treating and/or cleaning the surfaces of wooden articles and structural members of houses and buildings, resulting in keeping original and comfortable touch of wood on the surfaces of articles, etc., also after being treated therewith, in being sanitary and hygienic and in exhibiting various natural pharmaceutical effects. The second object is providing wooden building materials impregnated with the treatment agents mainly comprising natural materials, resulting in matching with ecological- and natural-oriented life without spoiling natural appearance of wood, in ensuring air permeability for natural breathing of wooden building materials, and in being stable long and endurable against long-term use under peculiar humid climates.

THE PRESENT INVENTION

The present invention relates to treatment agent for surface-treating and/or cleaning for articles and structures disposed in and/or assembled into houses and buildings, the characteristic is that the agent contains cineole $C_{10}H_{18}O$.

Eucalyptus oil mainly containing cineole may be also utilized for the treatment agent. Japan wax, beeswax, carnauba wax or emulsifier is applicable to the additives of the agent.

Wooden building materials like floorboards surface-treated by natural materials according to the present invention is impregnated and/or sprayed with the treatment agent containing cineole on the surfaces thereof.

According to the present invention characterizing in that treatment agent contains cineole, articles and structural members disposed in and/or assembled into houses and buildings may exhibit pharmaceutical effects based on cineole after the agent is impregnated thereon, resulting in being useful and unstimulative to the skin of human beings and in enabling surface-treating and washing sanitarily and hygienically.

Adopting eucalyptus oil mainly containing cineole actualizes the treatment agent made from complete natural materials. The agent including additives like Japan wax, beeswax, carnauba wax or emulsifier may display not only the pharmaceutical effects of cineole but glossing effect, water-repellentability, emulsifying effect and enhancing effect of cleaning power peculiar to each additive, resulting in increasing kinds of the function of agent.

Wooden building materials like floorboards impregnated with the treatment agent containing cineole may exhibit several natural pharmaceutical effects and may provide original and comfortable touch of wood and sanitary and hygienic circumstances appropriate to the walkers and residents. Moreover, the wooden building materials impregnated and sprayed with the treatment agent would not spoil natural breathing and humid controllability thereof, resulting in endurance of long-term use matching with peculiar humid climates, besides in maintenance of protecting effects from molding and from infesting with insects and air permeability of the floorboards, etc. themselves.

PREFERABLE EMBODIMENT

The treatment agent for surface-treating and/or cleaning according to the present invention is disclosed in detail by referring to the preferable examples as well as wooden building materials impregnated therewith. The wood keeping a natural state is preferable to flooring materials because it is ecological and quite unstimulative against the skin of a human being and sends forth the comfortable scent of wood. Needless to say, it is indispensable that floorboards walked barefoot especially have smooth and comfortable touch and are sanitary and hygienic.

Japanese cypresses and elm trees have been often used for wooden floorboards, in addition, recently eucalyptuses have been also attracted a great deal of attention therefor. Though there are many kinds of eucalyptus, it is said that Tasmanian oaks growing in Tasmania located in cold region of Australia are most suitable for building materials above all. They will be especially suited to floorboards, because they have fine grain of wood and are rather hard.

Not only Tasmanian oaks but eucalyptuses which can present some kinds of natural pharmaceutical effects as described after are useful and sanitary for barefooted walking, therefore, the floorboards made thereof are especially suitable for living in the humid climate, i.e., for a mode of Japanese life. Moreover, it has been experimentally and scientifically confirmed that eucalyptuses themselves are free from rottenness and damage of termites. And it is well-known that the tree- and leaf-sap of eucalyptuses have pharmaceutical effects. In particular, from the leaf sap thereof eucalyptus oil can be practically extracted.

The aroma of eucalyptus oil floating in the air generates atmosphere just as if they were in the natural world and/or were strolling about through woods. The eucalyptus oil has disinfection effects, e.g., decreasing germ and sterilizing as well as protecting effects from molding and infesting with insects. Lately in Japan, it has been often utilized as medicine or its additives in view of protecting effects from athlete's foot, pollinosis, abrasion, incised wounds and a cold. It also has deodorizing and cleaning effects and is, on the whole, unstimulative to skin and hygienic, then it is sometimes added to or applied to cooking spices, cosmetics and camphor.

According to the above, it is obviously comprehensible that the eucalyptuses themselves are useful to human bodies and floorboards, and that they are one of the most optimum materials for floors and corridors of gymnasiums and houses on which there are many opportunities for walking barefooted. A main object of the present invention is to provide more sanitary wooden building materials by means of the application of eucalyptuses to, e.g., floorboards and open wooden verandas which often keep in touch with the skin and by means of the impregnation of the after-mentioned treatment agent mainly made of eucalyptus oil on the surface thereof. Needless to say, Japanese cypresses, cryptomerias, pine trees, Japanese oaks and zelkova trees, etc., are available to wooden building materials as a substitute for eucalyptuses mentioned above. The promotion of utilization of the lumber thereof thinned out contributes to resuscitate woods, preventing trees from over-luxuriating.

The detail of eucalyptus oil is hereby described: Eucalyptus oil displays pharmaceutical effects mentioned above, and the main chemical component is cineole $C_{10}H_{18}O$. The cineole content is not always constant even in 100% pure eucalyptus oil, and the percentage thereof is generally 60% to 90% at most. Incidentally, the cineole mainly consists of 1,8-cineole, and the residual composes of other kinds of chemical substances like $\alpha$-pinene, $\alpha$-terpineol and/or limonene, which are all innocuous substances existing in the natural world.

Eucalyptus materials and Japanese cypresses, etc., mentioned before are sawn to boards of 10 to 20 millimeters thick for manufacturing floorboards with appropriate sizes. Floorboards are cut into, for instance, rectangular plates of 10 centimeters wide, 0.5 to 2 meters long, and if necessary, lapping portions for joining are formed in order not to make any clearance between the floorboards adjoined each other when they are disposed on the floor. Eucalyptus oil may be impregnated on walking surfaces of floorboards only, however, needless to say, the uneven planes for engaging with joining portions each other and the rear surfaces thereof may be also impregnated. It is easy to manufacture floorboards by impregnating eucalyptus oil on the surface thereof in the way of soaking boards of desired sizes in the oil, which result in providing various natural pharmaceutical effects, i.e., preservability and protectability from molding based on the effects of eucalyptus oil.

The impregnation of eucalyptus oil or cineole on the surfaces of floorboards is also performed by rubbing or spraying. The surfaces thereof do not look like to be covered with films, i.e., not giving the sense of touch and impressions that the surfaces thereof appear to be coated with something. If floorboards, corridors and wide wooden verandas, etc., are made of eucalyptuses, they result in being assembled with wooden building materials exhibiting pharmaceutical effects of eucalyptuses in cooperation with eucalyptus oil impregnated on the surface thereof and being useful to and unstimulative for human bodies. Even if other lumbers like Japanese cypresses, etc., are used as wooden building materials instead of eucalyptuses, those impregnated with eucalyptus oil or cineole have pharmaceutical effects, similarly to the case of using eucalyptuses.

As a matter of course, the air permeability which would not spoil natural breathing of wooden materials is maintained, as a result, ecological building materials having humid controllability and being endurable against long-term use are obtained. There is not so much difference apparently between the surfaces after impregnated and those prior to done, besides uncomfortable odor is hardly sent forth. They still remain natural touch in barefooted walk and also provide sterilizing effect. It has been confirmed that floorboards themselves are able to display not only preservability but respectable water proof and wear-proof to some extent.

Cleaning effect based on eucalyptus oil, namely effect as cleaner and/or solvent, can be displayed, making easy to keep surfaces clean without leaving stains of wine and coffee, etc. The treatment agent can be also utilized as wiping solution for cleaning. Since the solution according to the invention never forms coating films and layers, surfaces of floorboards are finished leaving natural and original surface of wood. The gloss of materials, therefore, will appear for long-term use, resulting in making the treated surfaces more tasteful, besides, in keeping the atmosphere in rooms at appropriate humidity by means of natural balancing effect based on the breathing of wood.

It is needless to describe again that the above-mentioned various effects are exhibited by the function of cineole $C_{10}H_{18}O$ contained in eucalyptus oil, of course, the proper quantity of Japan wax may be added to the solution made from either eucalyptus oil or cineole. Japan wax prevents cineole or eucalyptus oil from volatilizing from the surfaces treated thereby. Accordingly, the durability of effects based on eucalyptus oil and the like is guaranteed long and glossing the original surface of materials is promoted. In this case, the additional quantity thereof should be substantially restricted to 20% to 30% (weight ratio) so as not to interrupt the effects and functions of the solution mainly containing cineole.

As beeswax, carnauba wax and rice bran wax are natural materials, they are applicable to additives or substitutes for Japan wax mentioned above. They have a merit to give water-repellentability to the treated surfaces. Especially, beeswax promotes the durability of effects which eucalyptus oil and the like possess.

Moreover, nonionic surface active agent, which is emulsifier promoting washing effect, may be also added to the treatment agent. The additional quantity thereof is chosen e.g., 2% to 5% at most. Sorbitan emulsifier mixed beef tallow with sorbitan, milk casein, lecithin, beef tallow emulsifier and coconut emulsifier are also available.

In manufacturing wooden building materials, surfaces of which are treated by impregnating or infiltrating treatment agent, it should be considered that the melting point of cineole $C_{10}H_{18}O$ is approximately 1° C. Therefore, under the condition that the treatment agent is kept at about 30° C. preferably, the impregnation or infiltration thereof is performed by soaking wooden building materials like floorboards in liquid thereof for 3 seconds or more. In case of impregnating the walking surfaces only of floorboards, they are floated on the agent with the rear surface thereof upward, i.e., soaking one side only. Processing for soaking is normally done once, however, it may be repeated any number of times according to circumstances.

In the above-mentioned description, not only eucalyptus materials but Japanese cypresses, cryptomerias, pine trees, Japanese oaks and zelkova trees have been shown as original materials for wooden building materials, e.g., floorboards, besides the aforesaid solution is also applicable to elm trees. If eucalyptus oil or cineole liquid is impregnated on the exposed surfaces of wooden structural members assembled into the houses already constructed like pillars, floors, sills, beams, openwork screens above the sliding partitions between two rooms, and/or furniture like desks and chests of drawers, they can exhibit various pharmaceutical effects which include disinfection effects for decreasing germ and sterilizing, anti-bacterial effects, protecting effects from molding and from infesting with insects and sanitary effects like deodorizing and cleaning effects suitable for skin and bare feet, moreover, chemical and physical effects like waterproofing and the durability against rotting and wearing, and controllability of humidity.

In the case that the solution is impregnated on wooden materials with coarse grain like cryptomerias, it is often desirable that the wax content is much. When treatment agent is applied to floors and pillars, etc., already assembled into houses and to furniture, the impregnating operation thereof is not different from ordinary waxing work and controlling the temperature thereof is generally unnecessary.

As aforesaid, it is clear that cineole $C_{10}H_{18}O$ is effective as the solution treating surfaces of wooden building materials like floorboards and open wooden verandas. The cineole itself is suitable for impregnating solution similarly to eucalyptus oil. Cineole having a little camphoric odor is remarkably stable substance chemically, in result, the above-mentioned additives like Japan wax, etc., are also to be added thereto similarly to the case of adding them to eucalyptus oil. Supplying markets with various treatment agents providing appropriate quantity of additives which matches with the characteristic of each wooden material to be impregnated enlarges the range of consumers' choice in consideration of its chemical components and kind of wood materials applied to.

The treatment agent is used by rubbing, mopping or wiping with a piece of cloth soaked thereinto or by spraying itself, and such working operations are selected properly corresponding to objects when treating or washing. The above-mentioned shows the case that the treatment agent is applied to wooden building materials, however, needless to say, it is also applicable to wooden floors and furniture like desks, chests of drawers and wooden others in houses.

In addition, the treatment agent is also usable to non-wooden building materials, namely, articles and structures disposed in and/or assembled into houses and buildings like vinyl coated floors, to surfaces of carpets and tatami mats made of knitted rush, moreover, to interior materials for houses and to inner surfaces of shoes and insoles. The surfaces of tatami mats wiped and/or sprayed with the treatment agent would not be clammy also after treated, and protecting effect from infesting with insects and anti-bacterial effect prevent ticks from breeding and sundry bacteria from propagating in the mats.

The treatment agent is also applicable to surfaces of floorboards made of vinyl chloride panels and marble panels. In both cases, aforesaid various pharmaceutical effects according to the invention can be displayed. Effects in sanitation and in durability increase, besides termites result in seldom swarming about by means of insect repellent effect of the agent.

Incidentally, cineole $C_{10}H_{18}O$ is bicyclic monoterpene equivalent to ether in terpine molecule, and is stable substance chemically, as aforesaid, never changes in quality even if it is mixed with other additives. Such cineole can be also generated from terpine $C_{10}H_{20}O_2$, namely, it is well-known that cineole is obtained by means of dehydrating terpine after boiling by acids. Therefore, the cineole made from terpine is usable to the solution instead of eucalyptus oil.

Some examples of impregnant and/or washing solution as treatment agent are given in the following Table 1 and Table 2. The content and its mix ratio are only one instance, therefore, they can be changed properly according to purposes. In addition, adding eucalyptus oil to soap and detergents for food, tableware, cloths and furniture, of course, enables to display its pharmaceutical effects. Incidentally, Example 1 and 2 are for impregnation, and Example 3 is emulsion for rubbing. Example 4 is useful for soaking and spraying, Example 5 and 6 for wiping and spraying, and Example 7 for spraying.

TABLE 1

| CONTENTS | % | EFFECTS |
| --- | --- | --- |
| EXAMPLE 1 | | |
| eucalyptus oil | 90 | various effects disclosed above |
| Japan wax | 5 | glossing |
| | | promoting the durability of eucalyptus oil |
| beeswax | 5 | glossing, water-repellentability |
| | | promoting the durability of eucalyptus oil |
| EX. 2 | | |
| eucalyptus oil | 90 | referring to Example 1 |
| Japan wax | 5 | referring to Example 1 |
| carnauba wax | 5 | remarkable water-repellentability |
| EXAMPLE 3 | | |
| eucalyptus oil | 30 | referring to Example 1 |
| Japan wax | 5 | referring to Example 1 |
| carnauba wax | 5 | referring to Example 2 |
| nonionic surface active agent | 3 | emulsifying effect, cleaning |
| water | 57 | diluent |
| | | material for giving incombustibility |
| | | suppressing odor |
| EX. 4 | | |
| eucalyptus oil | 10 | referring to Example 1 |
| nonionic surface active agent | 3 | referring to Example 3 |
| water | 87 | referring to Example 3 |

TABLE 2

| CONTENTS | % | EFFECTS |
| --- | --- | --- |
| EXAMPLE 5 | | |
| eucalyptus oil | 30 | referring to Example 1 |
| Japan wax | 5 | referring to Example 1 |
| carnauba wax | 5 | referring to Example 2 |
| rice bran wax | 1 | glossing, water-repellentability improving working property against tatami mat |
| beeswax | 2 | referring to Example 1 |
| sorbitan emulsifying agent substitute; milk casein lecithin beef tallow emulsifier coconut emulsifier | 3 | emulsifying effect, cleaning |
| water | 54 | referring to Example 3 |
| EXAMPLE 6 | | |
| eucalyptus oil | 15 | referring to Example 1 |
| Japan wax | 3 | referring to Example 1 |

TABLE 2-continued

| CONTENTS | % | EFFECTS |
| --- | --- | --- |
| carnauba wax | 2 | referring to Example 2 |
| rice bran wax | 1 | referring to Example 5 |
| coconut emulsifier | 1 | emulsifying effect, cleaning |
| beef tallow emulsifier substitute; milk casein lecithin | 1 | emulsifying effect, cleaning |
| water | 77 | referring to Example 3 |
| EX. 7 | | |
| eucalyptus oil | 10 | referring to Example 1 |
| medical ethanol or industrial ethanol | 60 | disinfection effects |
| water or ion exchange water | 30 | referring to Example 3 |

More detailed explanation is as follows: When Example 5 is used as wiping solution, wooden walls or wooden floors are treated with mops or floorcloth soaked with it. In this example, milk casein, etc., are available as a substitute for sorbitan emulsifier mixed beef tallow with sorbitan. The treatment agent of Example 5 is characterized that it consists of natural materials only except the case that it is mixed with beef tallow emulsifier adding acetic acid or coconut emulsifier. Adding casein or lecithin to the agent presents a chance for insects to eat, however, there is no fear of their gathering because the quantity of addition is a very few and protecting effect from infesting with insects and antibacterial effect are remarkably exhibited by eucalyptus oil.

Example 6 also consists of natural materials only, therefore, is suitable for treatment agent for rubbing surfaces of tatami mats since it contains rice bran wax. Example 7 is very proper for cleaner because it is provided with noticeable protecting effect from molding. The agent including medical ethanol is suitable for cleaning chopping boards and knives because of being innocuous for human beings even if it enters the bodies. In the case that industrial ethanol is added to agent, it should be used for cleaning walls etc., of kitchen and bathroom. The reason why ion exchange water is used as diluent is that such treatment agent often touches human bodies.

What is claimed is:

1. A treatment composition for surface treating by disinfecting articles used in houses and buildings consisting essentially of:

eucalyptus oil containing cineole and/or cineole ($C_{10}H_{18}O$), as a disinfecting agent included at least 10% by weight, and, a wax selected from the group consisting of Japan wax, carnauba wax and combinations thereof for limiting a volatility of the eucalyptus oil.

2. The treatment agent of claim 1 further comprising beeswax.

3. The treatment agent according to claim 1 further comprising a natural emulsifying agent selected from the group consisting of natural milk casein, lecithin and combinations thereof.

* * * * *